(12) United States Patent
Georgeson

(10) Patent No.: US 9,500,606 B2
(45) Date of Patent: Nov. 22, 2016

(54) VISUAL INDICATOR OF AN EXPOSED GAMMA SOURCE

(71) Applicant: The Boeing Company, Chicago, IL (US)

(72) Inventor: Gary E. Georgeson, Federal Way, WA (US)

(73) Assignee: The Boeing Company, Chicago, IL (US)

( * ) Notice: Subject to any disclaimer, the term of this patent is extended or adjusted under 35 U.S.C. 154(b) by 150 days.

(21) Appl. No.: 14/499,995

(22) Filed: Sep. 29, 2014

(65) Prior Publication Data

US 2016/0091442 A1    Mar. 31, 2016

(51) Int. Cl.
| | | |
|---|---|---|
| *G01N 23/223* | (2006.01) | |
| *G01T 1/00* | (2006.01) | |
| *G01T 1/16* | (2006.01) | |
| *G01T 1/169* | (2006.01) | |

(52) U.S. Cl.
CPC .............. *G01N 23/223* (2013.01); *G01T 1/00* (2013.01); *G01T 1/16* (2013.01); *G01T 1/169* (2013.01)

(58) Field of Classification Search
CPC .......................... G01N 33/533; G01N 33/588
See application file for complete search history.

(56) References Cited

U.S. PATENT DOCUMENTS

| 3,600,574 | A | 8/1971 | Glaza |
|---|---|---|---|
| 7,902,524 | B2 | 3/2011 | Safai et al. |
| 7,925,452 | B2 | 4/2011 | Safai et al. |
| 2007/0117208 | A1 | 5/2007 | Niwa |
| 2007/0280423 | A1* | 12/2007 | Schmidt .................. A61B 5/103 378/165 |

FOREIGN PATENT DOCUMENTS

| EP | 2977791 A1 | 1/2016 |
|---|---|---|
| JP | 2011056131 A | 3/2011 |
| WO | 2013184204 A2 | 12/2013 |

OTHER PUBLICATIONS

Zyga, Lisa, "Researchers Prepare Cheap Quantum Dot Solar Paint," Nanotechnoloty/Nanophysics, Dec. 16, 2011, downloaded from <http//phys.org/print243240490.html> on Sep. 29. 2014, pp. 1-3.
Kang et al., "CdTe quantum dots and polymer nanocomposites for x-ray scintillation and imaging," Applied Physics Letters 98, 181914, May 6, 2011, pp. 1-3.
European Patent Office; Extended European Search Report for European Patent Application No. 15181526.3 dated Mar. 4, 2016, 11 Pages.

* cited by examiner

*Primary Examiner* — Hoon Song
(74) *Attorney, Agent, or Firm* — Charles L. Moore; Moore & Van Allen PLLC

(57) ABSTRACT

A device for indicating a presence of X-rays or gamma rays may include a visual indicator. The visual indicator may include a material and a plurality of quantum dots adhering to the material or disposed in the material. The quantum dots may be exposed on a surface of the material opposite an object when the material is attached to the object. The quantum dots fluoresce in response to the quantum dots being exposed to X-rays or gamma rays.

20 Claims, 6 Drawing Sheets

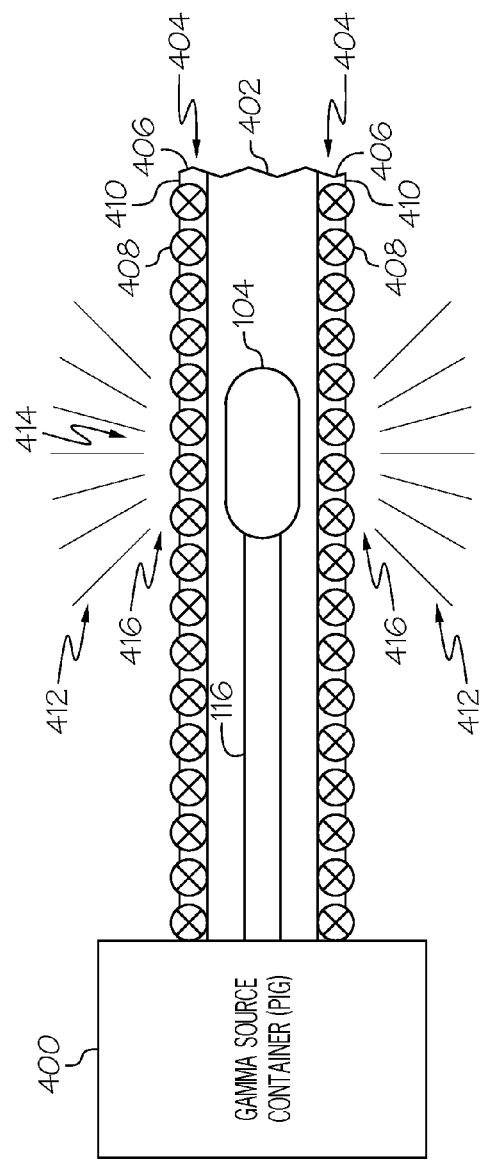
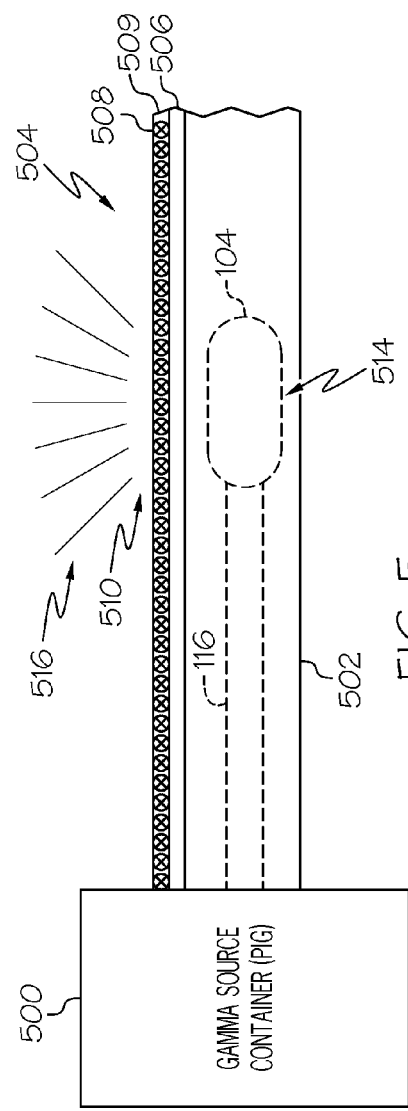

VISUAL INDICATOR OF AN EXPOSED GAMMA SOURCE

FIELD

The present disclosure relates to gamma sources usable for inspection, medical purposes and other purposes, and more particularly to a system including a including a visual indicator of an exposed gamma source.

BACKGROUND

X-rays or gamma rays from a radioactive source or gamma radiation source have uses in industry and medical application. For example, X-rays or gamma rays may be used in industry for non-destructive testing of parts or components by X-ray inspection. A workpiece under inspection may be placed between an X-ray source or gamma ray source and a detector to inspect the workpiece for any abnormalities. In another non-destructive test arrangement, the detector may also be placed to receive X-rays or gamma rays that are back-scattered from the workpiece to detect any abnormalities. Similarly, X-rays and other radioactive materials are used in medical science for both diagnosis and therapeutic purposes. However, exposure to X-rays or gamma rays, or prolonged or repeated exposure to even low intensity X-rays or gamma rays may be harmful. X-rays are invisible to the human eye, so users of X-ray equipment wear sensors or monitors to indicate that X-rays are on and/or wear film badges that show X-ray exposure has taken place. A warning indicator, such as an illuminated sign or other alerting device is typically operated to warn users and others that such equipment is active or in use. Under some circumstances, however, such warning devices may not function properly or may be inoperable for whatever reason, and film badges and similar detection devices may only identify exposure after the exposure has occurred. Accordingly, there is a need to provide an arrangement or mechanism that provides an instantaneous visual indication that an X-ray source or gamma source is exposed or unshielded and that is not subject to the disadvantages of devices that may require electrical power for illumination and operation of a switch or other mechanism when the X-ray source or gamma source is active, exposed or not properly stored in a shielded container.

SUMMARY

In accordance with an embodiment, a device for indicating a presence of X-rays or gamma rays may include a visual indicator. The visual indicator may include a material and a plurality of quantum dots adhering to the material or disposed in the material. The quantum dots may be exposed on a surface of the material opposite an object when the material is attached to the object. The quantum dots fluoresce in response to the quantum dots being exposed to X-rays or gamma rays.

In accordance with another embodiment, a system for non-destructive testing may include a gamma source and a shielded container for storing the gamma source when not performing a non-destructive test. The system may also include a flexible guide sleeve extending from the shielded container through which the gamma source may be extended from the shielded container for performing inspections. A flexible source positioning rod or cable may be attached at one end to the gamma source for extending the gamma source through the guide sleeve and for retrieving the gamma source back within the shielded container. A port may be formed in the shielded container through which the flexible source positioning rod may extend and attach to the gamma source for extending the gamma source through the flexible guide sleeve. A visual indicator may be attached to at least one of the shielded container and the flexible guide sleeve. The visual indicator may include a material and a plurality of quantum dots adhering to the material or disposed in the material. The quantum dots may be exposed on a surface of the material opposite an object when the material is attached to the object. The object may be either the shielded container, flexible sleeve guide or both. The quantum dots fluoresce in response to the quantum dots being exposed to X-rays or gamma rays.

In accordance with a further embodiment, a method for indicating a presence of X-rays or gamma rays may include providing a visual indicator. Providing the visual indicator may include providing a material and providing a plurality of quantum dots adhering to the material or disposed in the material. The quantum dots may be exposed on a surface of the material opposite an object when the material is attached to the object. The quantum dots fluoresce in response to the quantum dots being exposed to X-rays or gamma rays.

BRIEF DESCRIPTION OF THE SEVERAL VIEWS OF DRAWINGS

The following detailed description of embodiments refers to the accompanying drawings, which illustrate specific embodiments of the disclosure. Other embodiments having different structures and operations do not depart from the scope of the present disclosure.

FIG. 4B is a schematic diagram of the exemplary gamma source storage container and cross-sectional view of the guide sleeve in FIG. 4A illustrating the visual indicator identifying the location of the gamma source within the guide sleeve in accordance with an embodiment of the present disclosure.

FIG. 5 is a schematic diagram of an exemplary gamma source storage container and guide sleeve including the exemplary visual indicator of FIG. 3 for indicating the location of the gamma source within the guide sleeve in accordance with an embodiment of the present disclosure.

DETAILED DESCRIPTION

Figure 1A:
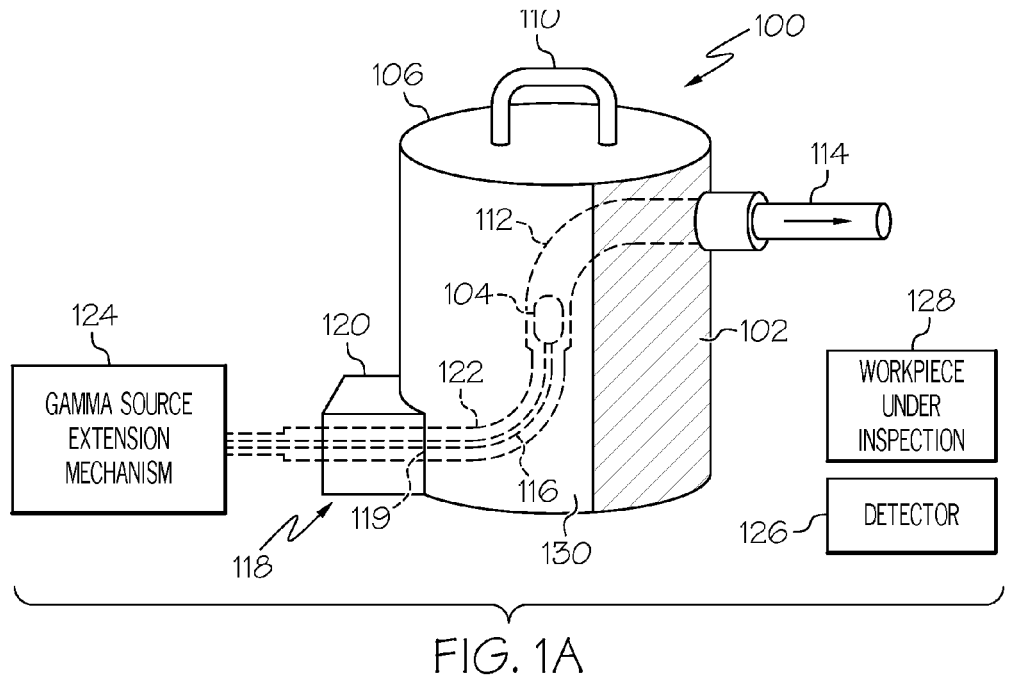
FIG. 1A is a schematic diagram of an example of a gamma source inspection system including a visual indicator showing that the gamma source is stored and not exposed in accordance with an embodiment of the present disclosure.

The following detailed description of embodiments refers to the accompanying drawings, which illustrate specific embodiments of the disclosure. Other embodiments having different structures and operations do not depart from the scope of the present disclosure. Like reference numerals may refer to the same element or component in the different drawings.

FIG. 1A is a schematic diagram of an example of a gamma source inspection system 100 including a visual indicator 102 showing that the gamma source 104 is stored and not exposed in accordance with an embodiment of the present disclosure. The gamma source inspection system 100 may be a non-destructive testing system or similar inspection system. The system 100 may include a container 106 for storing the gamma source 104 when not performing an inspection or non-destructive test. The container 106 may be a shielded container. The gamma source 104 may include a radioactive material or isotope that emits X-rays or gamma radiation or rays 108 (FIG. 1B) that may pass through certain objects for internal inspection of the objects or back-scattered off an object or workpiece under inspection as described in more detail herein for inspection of the object or workpiece. As used herein, X-rays or gamma rays may be used interchangeably and either may generically refer to any radiation and particularly any radiation that may be harmful under certain circumstance to humans. Gamma source may also refer to any source of radiation that may be harmful to humans under certain circumstances.

The container 106 or shielded container may be a portable gamma source container 106 which may be referred to as a pig. The portable shielded container 106 may be portable for movement from one location to another for non-destructive testing or inspection of different workpieces or different components or parts of a larger assembly. The larger assembly may be, for example, a civil structure, such as a building, bridge or other civil structure, a vehicle, such as an aircraft, a ship or other vehicle or other assembly. The gamma source container 106 may include a handle 110 for carrying the container 106 by a person from one location to another. The container 106 may be constructed of a material that prevents X-rays or gamma-rays from passing or escaping outside of the container 106 when the gamma source 104 is withdrawn completely within the container 106 for storage. Examples of materials from which the shielded container 106 may be made may include but is not necessarily limited to lead, lead alloy, a material containing lead, such as leaded glass or any other material capable of blocking X-rays, gamma rays or similar radiation. Steel or concrete containers or barriers may also be used. The container 106 may also be made from lightweight material with a lead lining or lining of another material that blocks X-rays or gamma rays. In accordance with an embodiment, a sheath 112 may be disposed within the container 106 for containing the gamma source 104 when fully retracted and stored in the container 106. The sheath 112 may be made from a material that blocks X-rays or gamma rays.

The system 100 may also include a guide sleeve 114 extending from the shielded container 106 through which the gamma source 104 may be extended from the shielded container 106 for performing inspections. As described in more detail with reference to FIGS. 4A and 4B, the guide sleeve 114 may be a flexible guide sleeve or carrier hose that permits the guide sleeve 114 to be extended around corners or extended through a piping system, duct system or similar enclosed system or structure that can change direction and may have multiple angled turns or bends. The flexible guide sleeve 114 permits inspection of such systems or structures.

The system 100 may additionally include a source positioning rod 116. The source positioning rod 116 may be attached at one end to the gamma source 104 for extending the gamma source 104 through the guide sleeve 114 and for retrieving the gamma source 104 back within the container 106. The source positioning rod 116 may be a flexible positioning rod for bending around corners and making turns following any layout of the guide sleeve 114. The source positioning rod may be a flexible cable or other material capable of pushing the gamma source 104 as the source positioning rod 116 is feed into the flexible sleeve guide 114.

The system 100 may also include a port 118 or opening formed in the container 106 through which the flexible source positioning rod 116 extends and attaches to the gamma source 104 for extending the gamma source 104 through the flexible guide sleeve 114. The port 118 may include an enclosure 120 attached to a side of the container 106. The enclosure 120 may provide protection and sealing of an opening 119 in the container 106 for the source positioning rod 116 and prevent leakage of radiation from the gamma source 104. A conduit 122 may couple the port 118 to the sheath 112 that holds the gamma source 104 when stored in the container 106.

The system 100 may further include a gamma source extension mechanism 124. The gamma source extension mechanism 124 may extend and retract the flexible source positioning rod 116 for extending and retracting the gamma source 104 during an inspection process. The gamma source extension mechanism 124 may be a reel for winding the flexible source positioning rod 116.

The system 100 may also include a detector 126 configured to detect X-rays, gamma rays or similar radioactive radiation. In one inspection configuration, a workpiece 128 under inspection may be placed between the gamma source 104 and the detector 126. In another inspection configuration, the detector 126 may be positioned to detect X-rays, gamma rays or other radiation that is back-scattered from the workpiece 128.

The visual indicator 102 may be applied or attached to at least a portion of an exterior surface 130 of the container 106. In accordance with another embodiment, the visual indicator 102 may be attached or applied to the flexible guide sleeve 114. An exemplary embodiment with the visual indicator 102 attached or applied to the flexible guide sleeve 114 will be described with reference to FIGS. 4A and 4B and FIG. 5. In a further embodiment, a visual indicator may be applied to both the shielded container 106 and the flexible guide sleeve 114.

Figure 1B:
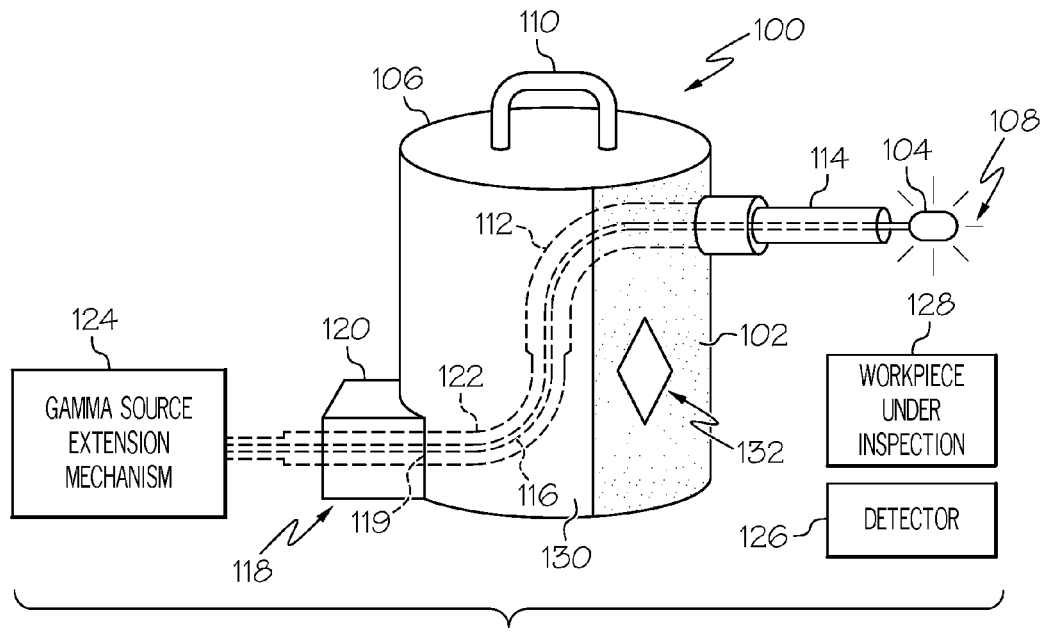
FIG. 1B is a schematic diagram of the exemplary gamma source inspection system of FIG. 1B with the visual indicator showing that the gamma source is exposed in accordance with an embodiment of the present disclosure.
Figure 2:
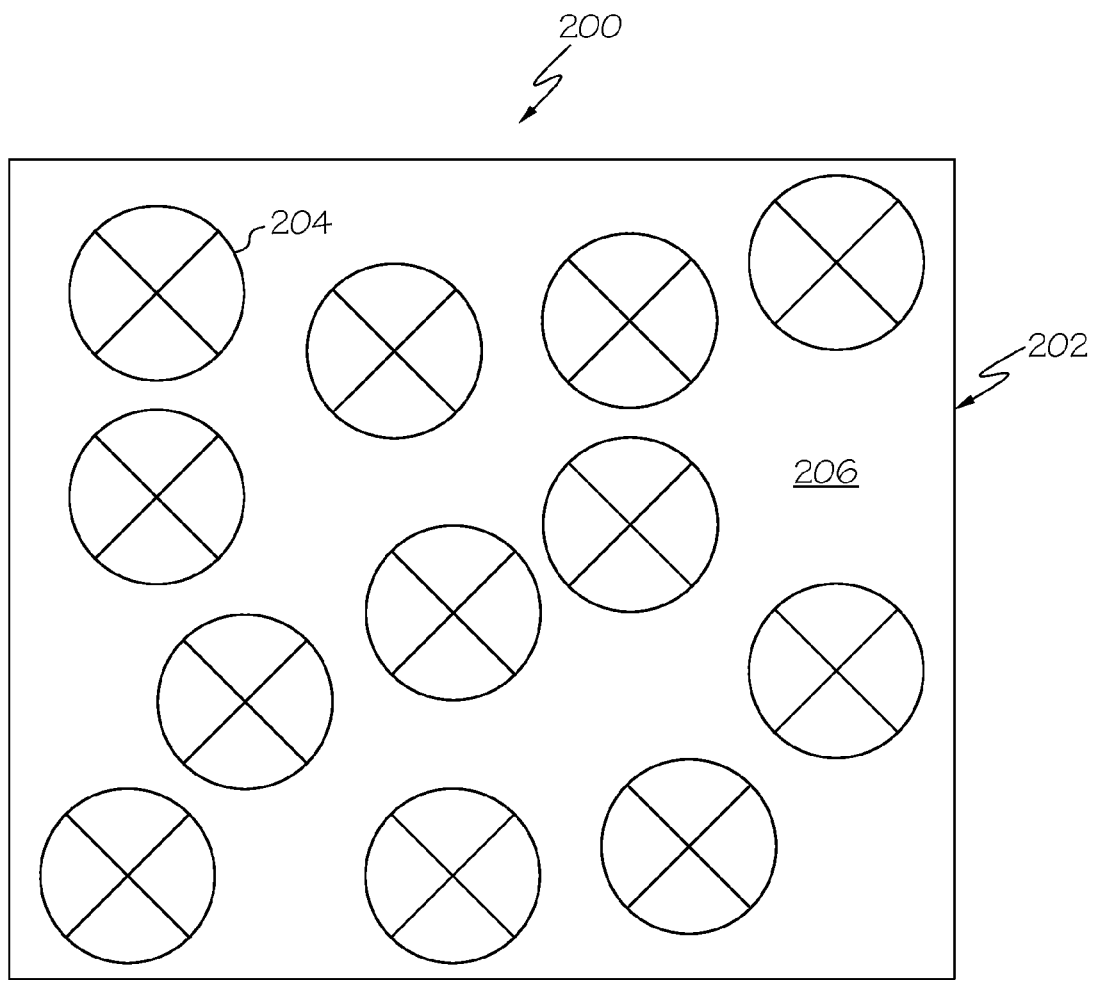
FIG. 2 is a detailed view of an example of a visual indicator 200 that may be used for the visual indicator in FIGS. 1A and 1B in accordance with an embodiment of the present disclosure.

Referring also to FIG. 2, FIG. 2 is a detailed view of an example of a visual indicator 200 that may be used for the visual indicator 102 in FIGS. 1A and 1B in accordance with an embodiment of the present disclosure. The visual indicator 200 may include a material 202 and a plurality of quantum dots 204 adhering to the material 202 or in some embodiments the quantum dots 204 may be disposed or mixed in the material 202. The quantum dots 204 may be exposed on a surface of the material 202 opposite an object, such as the container 106 in FIGS. 1A and 1B when the material 202 is attached to the object or container 106. The quantum dots 204 depicted in FIG. 2 are for illustrative and explanatory purposes and are not intended to represent an actual size, shape or structure of an actual quantum dot. A quantum dot is a nanocrystal made of semiconductor materials that are small enough to exhibit quantum mechanical properties. The quantum dots 204 fluoresce in the visible range in response to being exposed to X-rays or gamma rays. Thus, the quantum dots 204 convert X-rays or gamma rays to light radiation in the visible spectrum. Cadmium Tellurium (CdTe) quantum dots and quantum dot-based polymer nanocomposite materials have been found to be usable in X-ray scintillation and imaging applications. The CdTe quantum dots provide X-ray luminescence with highly advantageous characteristics for applications such as those described herein including high-resolution, fast decay, non-afterglow, high stopping power and superior spectral match to a charge coupled device (CCD) detector. Such characteristics indicate that CdTe nanocomposites are useful for nanophosphor X-ray imaging applications such as in the present disclosure. Quantum dots for use in applications such as those described herein are available from various sources including Evident Technologies, Inc., Troy N.Y.

The material 202 may be paint 206 or similar material and the quantum dots 204 may be mixed in the paint 206. The quantum dots may be mixed into a paint or coating in a concentration of about 0.01% to about 0.5% by weight. The selected concentration may be determined based on the visual intensity desired. The quantum dots 204 are added to the paint 206 in a sufficient concentration that the fluorescence will be obvious and clearly attract attention when the gamma source 104 is exposed and there is a distinct contrast in the visual indicator 102 between when the gamma source is exposed and when it is not. The paint 206 containing the quantum dots 204 may be sprayed or brushed on the container 106 or pig. The paint or coating does not have to be continuous. For example, the paint or coating may be applied in a predetermined pattern, such as dots or other pattern or geometric shape. The paint 206 containing the quantum dots 204 may be sprayed or brushed on a portion of the container 106, or the entire container 106 or pig may be painted with quantum dot paint 206. The paint or coating may also be applied by other techniques, such as those similar to ink jet printing.

Figure 3:
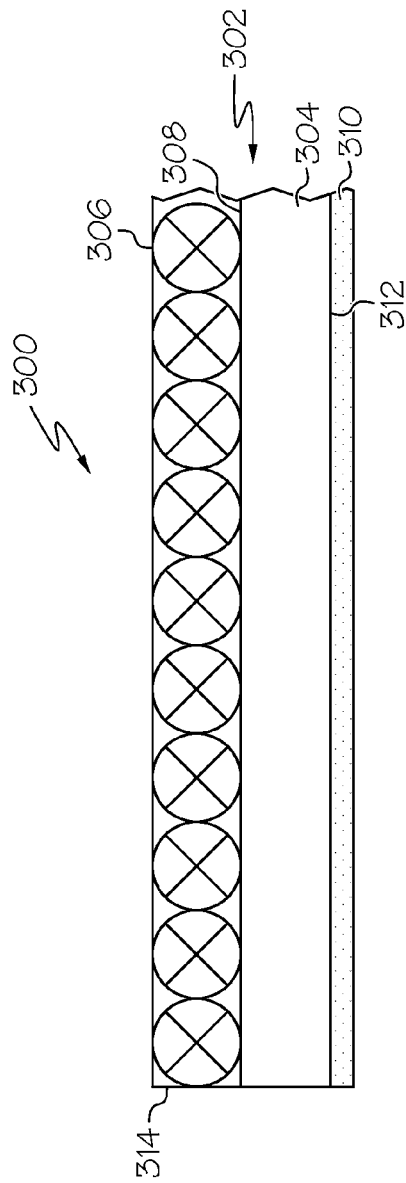
FIG. 3 is a side elevation view of an example of another visual indicator that may be used for the visual indicator in FIGS. 1A and 1B in accordance with an embodiment of the present disclosure.

FIG. 3 is a side elevation view of an example of another visual indicator 300 that may be used for the visual indicator 102 in FIGS. 1A and 1B in accordance with an embodiment of the present disclosure. The material 302 may include a tape 304 or sticker. A plurality of quantum dots 306 may be disposed or attached on one surface 308 of the tape 304 or sticker, and an adhesive layer 310 may be disposed or attached on an opposite surface 312 of the tape 304 or sticker for attaching the tape 304 or sticker to the object or container 106. The quantum dots 306 may be attached to tape 304 by an adhesive or other arrangement. In accordance with an embodiment, paint 314 containing quantum dots 306 may be brushed or sprayed on the tape 304.

Referring back to FIGS. 1A and 1B, the visual indicator 102 may be formed in a predetermined design 132, similar to that illustrated in FIG. 1B to alert a user in response to the gamma source 104 being exposed outside the container.

FIG. 1B is a schematic diagram of the exemplary gamma source inspection system 100 of FIG. 1A with the visual indicator 102 showing that the gamma source 104 is exposed in accordance with an embodiment of the present disclosure. Examples of the predetermined design 132 of the visual indicator 102 may include but are not necessarily limited to: the visual design changing color, for example, the fluorescing quantum dots may cause the visual indicator 102 to appear in much brighter colors and colors indicative of providing a warning or alert, such as red, yellow, orange or other bright attention drawing colors; the predetermined design may also be in the form of the symbol commonly used for alerting of a presence of a radiation hazard. The visual indicator 102 may also include clearly visible text, such as "RADIATION HAZARD", "EXPOSED GAMMA SOURCE", or similar text that may clearly convey the condition and provide situational awareness to the user.

Figure 4A:
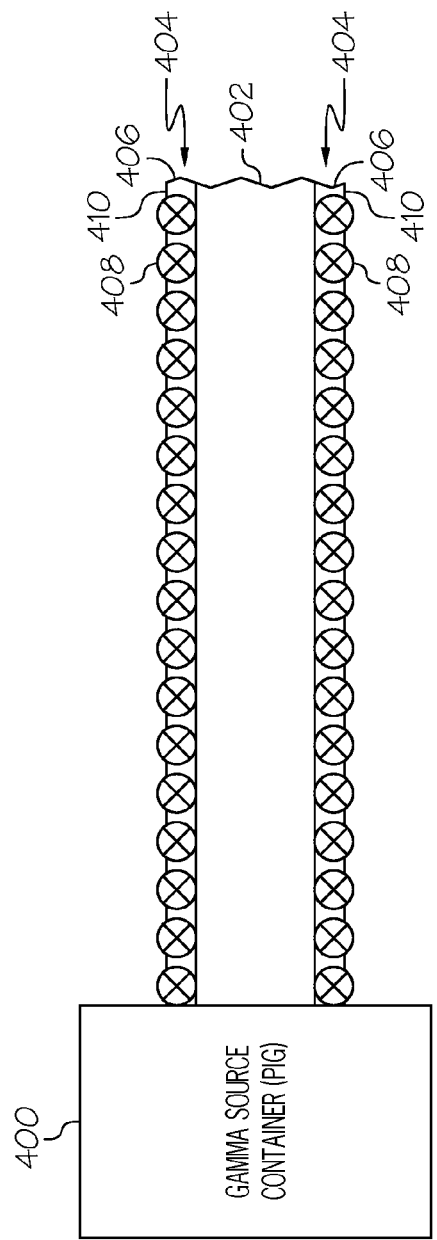
FIG. 4A is a schematic diagram of an example of a gamma source storage container and cross-sectional view of a guide sleeve including a visual indicator for indicating a location of the gamma source within the guide sleeve in accordance with an embodiment of the present disclosure.

FIG. 4A is a schematic diagram of an example of a gamma source storage container 400 and cross-sectional view of a guide sleeve 402 including a visual indicator 404 for indicating a location of the gamma source 104 within the guide sleeve 402 in accordance with an embodiment of the present disclosure. The gamma source container 400 and the guide sleeve 402 may be components of a gamma source inspection system similar to gamma source inspection system 100 in FIGS. 1A and 1B. The gamma source container 400 may be the same as the gamma source container 106 in FIGS. 1A and 1B and the guide sleeve 402 may be the same as the guide sleeve 114 in FIGS. 1A and 1B. The visual indicator 404 may be similar to the visual indicator 200 described with reference to FIG. 2 or visual indicator 300 described with reference to FIG. 3. Accordingly, the visual indicator 404 may include a material 406 and a plurality of quantum dots 408 in or on the material 406. The quantum dots 408 are exposed on a surface 410 of the material 406 opposite the guide sleeve 402 when the material 406 is attached to the guide sleeve 402. The quantum dots 408 will generate fluorescence 412 in response to the gamma source being outside of the container 400 and within the sleeve guide 402 exposing the quantum dots 408 to X-rays or gamma rays. FIG. 4B is a schematic diagram of the exemplary gamma source storage container 400 and cross-sectional view of the guide sleeve 402 illustrating the visual indicator 404 identifying the location 414 of the gamma source 104 within the guide sleeve 402 in accordance with an embodiment of the present disclosure. Only a portion 416 of the quantum dots 408 at the location 414 of the gamma source 104 within the sleeve guide 402 fluoresce or generate fluorescence 412 indicating the location 414 of the gamma source 104 within the guide sleeve 402 in response to exposure of the portion 416 of the quantum dots 408 to the X-rays or gamma rays emitted by the gamma source 104.

In one embodiment, substantially the entire sleeve guide 402 may be covered by the visual indicator 404. In another embodiment, the visual indicator 404 may be a single line or a plurality of lines of paint or tape including quantum dots 408 that extend substantially completely an extent or length of the guide sleeve 402. Ends of the guide sleeve 402, for example, proximate the container 400 and an opposite end of the guide sleeve 402 may not have the visual indicator 404 attached.

FIG. 5 is a schematic diagram of an exemplary gamma source storage container 500 and guide sleeve 502 including a visual indicator 504 for indicating the location of a gamma source 104 within the guide sleeve 502 in accordance with an embodiment of the present disclosure. The gamma source container 500 and the guide sleeve 502 may be components of a gamma source inspection system similar to gamma source inspection system 100 in FIGS. 1A and 1B. The gamma source container 500 may be the same as the gamma source container 106 in FIGS. 1A and 1B and the guide sleeve 502 may be the same as the guide sleeve 114 in FIGS. 1A and 1B. The visual indicator 504 may be similar to the visual indicator 300 described with reference to FIG. 3. Accordingly, the visual indicator 504 may include a tape 506 or sticker and a plurality of quantum dots 508 disposed or attached to an upper or outside surface of the tape 506. Similar to that described with reference to FIG. 3, the quantum dots 508 may be mixed in a material 509, such as paint or other material and the paint may be applied to the tape 506. The tape 506 may include an adhesive layer (not shown in FIG. 5 for purposes of clarity) on an opposite side of the tape 506 from the quantum dots 508. The adhesive layer may be similar to adhesive layer 310 in FIG. 3 for attaching the visual indicator 300 to the guide sleeve 502. Similar to that previously described, a portion 510 of the quantum dots 508 at a location 514 of the gamma source 104 within the guide sleeve 504 may fluoresce or generate fluorescence 516 to identify or indicate the location 514 of the gamma source 104 within the guide sleeve 504 in response to exposure of the portion 510 of the quantum dots 508 to the X-rays or gamma rays emitted by the gamma source 104.

Figure 6:
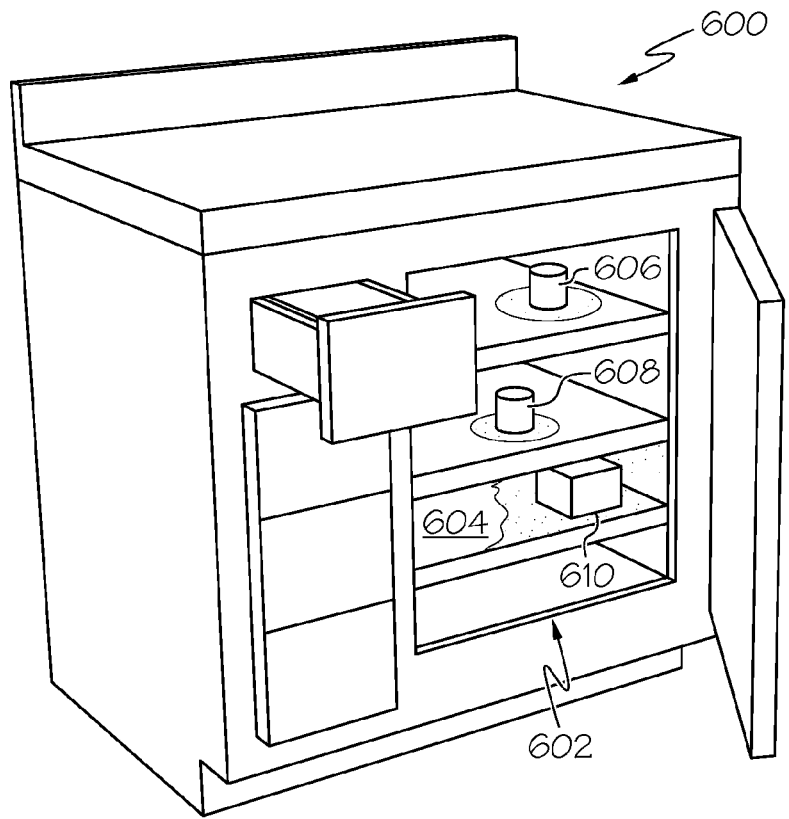
FIG. 6 is an illustration of a cabinet for storing radioactive isotopes in accordance with an embodiment of the present disclosure.

FIG. 6 is an illustration of a cabinet 600 for storing radioactive isotopes in accordance with an embodiment of the present disclosure. The cabinet 600 may be a shielded storage cabinet for medical isotopes or radioactive isotopes for other purposes. A visual indicator 602 similar to visual indicator 200 of FIG. 2 or visual indicator 300 of FIG. 3 may be applied to an interior 604 of the storage cabinet 600. Accordingly, an X-ray fluorescent paint containing quantum dots may be sprayed onto an interior 604 of the shielded storage cabinet 600. For example, foam holding isotope containers 606-610 may have quantum dot paint sprayed on them or quantum dot tape similar to that previously described may be applied to shelving of the storage cabinet 600. The quantum dots fluoresce in response to a radioactive isotope emitting gamma rays being placed in the cabinet 600. The visual indication provides situational awareness to anyone with access to the storage cabinet 600. The visual indicator 602 or indicators may glow a particular color, or the quantum dots may be applied in a predetermined pattern, such as a warning or radiation symbol by patterning the quantum dots when sprayed in paint on the cabinet 600 or applied as tape or a sticker.

Figure 7A:
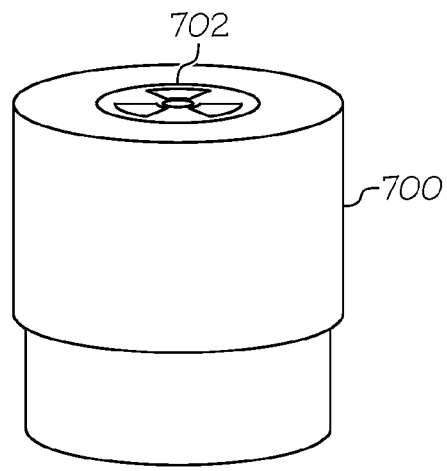
FIG. 7A is an illustration of a storage container for a radioactive isotope including a visual indicator showing that the storage container is currently containing the radioactive isotope in accordance with an embodiment of the present disclosure.
Figure 7B:
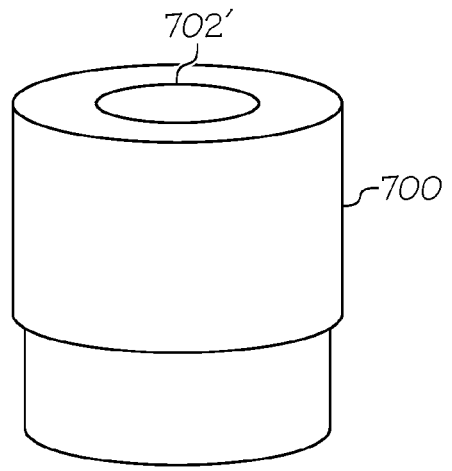
FIG. 7B is an illustration of the storage container of FIG. 7A with the visual indicator showing that the radioactive isotope is not within the storage container.

FIG. 7A is an illustration of a storage container 700 for a radioactive isotope including a visual indicator 702 showing that the storage container 700 is currently containing the radioactive isotope in accordance with an embodiment of the present disclosure. FIG. 7B is an illustration of the storage container of FIG. 7A with the visual indicator 702' showing that the radioactive isotope is not within the storage container 700. Accordingly, the visual indicator 702 will be configured to have an obvious difference in appearance to indicate whether or not the container 700 is containing a radioactive isotope. For example, the visual indicator 702 may fluoresce or glow with bright colors and/or the visual indicator may be in the pattern of a warning or radiation symbol to signify that the container 700 is currently containing the radioactive isotope compared to when the container 700 does not contain a radioactive isotope. The visual indicator 702 may be similar to visual indicator 200 described with reference to FIG. 2 or visual indicator 300 described with reference to FIG. 3.

Figure 8:
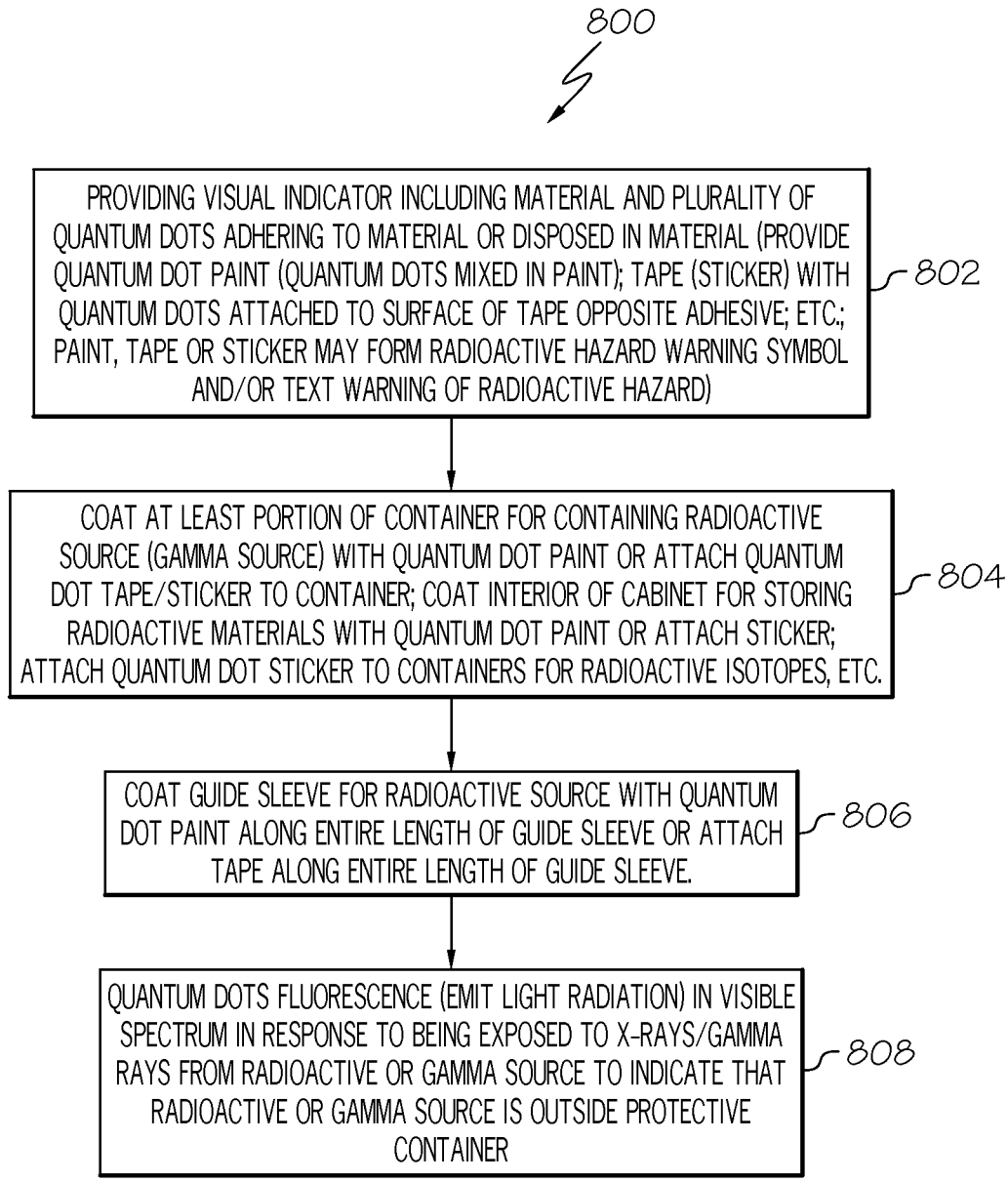
FIG. 8 is an example of a method of visually indicating a presence of X-rays or gamma rays or that a gamma source is exposed in accordance with an embodiment of the present disclosure.

FIG. 8 is an example of a method 800 of visually indicating a presence of X-rays or gamma rays or that a gamma source is exposed in accordance with an embodiment of the present disclosure. In block 802, a visual indicator may be provided including a material and a plurality of quantum dots adhering to the material or disposed in or on the material. Similar to that previously described, in one embodiment the quantum dots may be mixed in a paint. In another embodiment the quantum dots may be attached to a surface of tape or a sticker. Paint containing the quantum dots may be applied to the tape or sticker. The paint, tape or sticker may form a radioactive hazard warning symbol and/or may include text warning of a radioactive hazard.

In block 804, at least a portion of a container for storing a radioactive source or gamma source may be coated with the quantum dot paint or the quantum dot tape or sticker may be attached to the container. In another embodiment, an interior of a cabinet for storing radioactive materials may be coated with the quantum dot paint, or one or more quantum dot stickers or tape may be attached to the interior of the cabinet. In a further embodiment, quantum dot paint or a quantum dot sticker may be attached to an exterior of a container for storing radioactive isotopes similar to that previously described.

In block 806, a guide sleeve for the radioactive source or gamma source may be coated with a quantum dot paint along substantially an entire length of the guide sleeve. In another embodiment a quantum dot tape may be attached or applied along substantially the entire length of the guide sleeve.

In block 808, the quantum dots will fluoresce or emit light radiation in the visible spectrum in response to being exposed to X-rays or gamma rays from the radioactive source or gamma source to indicate that the radioactive or gamma source is outside of the protective container or is at a particular location within the guide sleeve similar to that previously described.

The flowchart and block diagrams in the Figures illustrate the architecture, functionality, and operation of possible implementations of systems and methods according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of embodiments of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to embodiments of the invention in the form disclosed. Many modifications and variations will be apparent to those of ordinary skill in the art without departing from the scope and spirit of embodiments of the invention. The embodiment was chosen and described in order to best explain the principles of embodiments of the invention and the practical application, and to enable others of ordinary skill in the art to understand embodiments of the invention for various embodiments with various modifications as are suited to the particular use contemplated.

Although specific embodiments have been illustrated and described herein, those of ordinary skill in the art appreciate that any arrangement which is calculated to achieve the same purpose may be substituted for the specific embodiments shown and that embodiments of the invention have other applications in other environments. This application is intended to cover any adaptations or variations of the present invention. The following claims are in no way intended to limit the scope of embodiments of the invention to the specific embodiments described herein.

What is claimed is:

1. A device for indicating a presence of X-rays or gamma rays, comprising:
   a visual indicator, the visual indicator comprising:
      a material; and
      a plurality of quantum dots adhering to the material, wherein the quantum dots are exposed on a surface of the material opposite an object when the material is attached to the object, the quantum dots fluorescing in response to the quantum dots being exposed to X-rays or gamma rays; and
   a container for storing a gamma source, the visual indicator is applied to at least a portion of an exterior surface of the container, wherein the quantum dots fluoresce in response to the gamma source being exposed outside of the container and the gamma rays emitted by the gamma source striking the quantum dots.

2. The device of claim 1, wherein the material comprises a paint and the quantum dots are mixed in the paint.

3. The device of claim 1, wherein the material comprises a tape or a sticker, the plurality of quantum dots being disposed on one surface of the tape or sticker and an adhesive being disposed on an opposite surface of the tape or sticker for attaching the tape or sticker to the object.

4. The device of claim 1, wherein the visual indicator is formed in a predetermined design to alert a user in response to the gamma source being exposed outside the container.

5. The device of claim 1, wherein the visual indicator is applied to a guide sleeve extending from the container for storing the gamma source, the guide sleeve for guiding movement the gamma source outside of the container, wherein the quantum dots fluoresce in response to the gamma source being outside of the container within the guide sleeve.

6. The device of claim 5, wherein the visual indicator is applied along a substantially complete extent of the guide sleeve and wherein only a portion of the quantum dots at a location of the gamma source within the guide sleeve fluoresce.

7. The device of claim 1, wherein the visual indicator is applied to one of at least the portion of the exterior surface of the container for storing the gamma source or along a substantially complete extent of a guide sleeve that extends from the container, the guide sleeve for guiding movement the gamma source outside of the container, wherein only a portion of the quantum dots at a location of the gamma source within the guide sleeve fluoresce indicating where the gamma source is outside of the container and within the sleeve guide.

8. The device of claim 1, wherein the container comprises a cabinet and the gamma source comprises a radioisotope, and wherein the visual indicator is applied to an interior of the cabinet for storing the radioactive isotope, the quantum dots fluorescing in response to the radioactive isotope emitting gamma rays being placed in the cabinet.

9. The device of claim 1, wherein the visual indicator is applied to an exterior of the container that is configured for storing a radioactive isotope, the visual indicator being configured to indicate whether or not the container is storing the radioactive isotope.

10. A system for non-destructive testing, comprising:
   a gamma source;
   a shielded container for storing the gamma source when not performing a non-destructive test;
   a flexible guide sleeve extending from the shielded container through which the gamma source may be extended from the shielded container for performing inspections;
   a flexible source positioning rod attached at one end to the gamma source for extending the gamma source through the guide sleeve and for retrieving the gamma source back within the shielded container;
   a port formed in the shielded container through which the flexible source positioning rod extends and attaches to the gamma source for extending the gamma source through the flexible guide sleeve;
   a visual indicator attached to at least one of the shielded container and the flexible guide sleeve, the visual indicator comprising:
      a material; and
      a plurality of quantum dots adhering to the material, wherein the quantum dots are exposed on a surface of the material opposite an object when the material is attached to the object, the quantum dots fluorescing in response to the quantum dots being exposed to X-rays or gamma rays.

11. The system of claim 10, wherein the visual indicator is applied to at least a portion of an exterior surface of the container for storing a gamma source, wherein the quantum dots fluoresce in response to the gamma source being exposed outside of the container and the gamma rays emitted by the gamma source striking the quantum dots.

12. The system of claim 10, wherein the visual indicator is applied along a substantially complete extent of the guide sleeve and wherein only a portion of the quantum dots at a location of the gamma source within the guide sleeve fluoresce.

13. The system of claim 10, wherein the material comprises paint and the quantum dots are mixed in the paint.

14. The system of claim 10, wherein the material comprises a tape or a sticker, the plurality of quantum dots being disposed on one surface of the tape or sticker and an adhesive being disposed on an opposite surface of the tape or sticker for attaching the tape or sticker to the object.

15. A method for indicating a presence of X-rays or gamma rays, comprising:
providing a visual indicator, providing the visual indicator comprising:
providing a material; and
providing a plurality of quantum dots adhering to the material, wherein the quantum dots are exposed on a surface of the material opposite an object when the material is attached to the object, the quantum dots fluorescing in response to the quantum dots being exposed to X-rays or gamma rays, wherein providing the visual indicator comprises attaching the visual indicator to at least a portion of an exterior surface of a container for storing a gamma source, wherein the quantum dots fluoresce in response to the gamma source being exposed outside of the container and the gamma rays emitted by the gamma source striking the quantum dots.

16. The method of claim 15, wherein the providing the visual indicator comprising forming the visual indicator in a predetermined design to alert a user in response to the gamma source being exposed outside the container.

17. The method of claim 15, wherein providing the material comprises providing a tape or sticker, the plurality of quantum dots being disposed on one surface of the tape or sticker and an adhesive being disposed on an opposite surface of the tape or sticker for attaching the tape or sticker to the container.

18. A method for indicating a presence of X-rays or gamma rays, comprising:
providing a visual indicator, providing the visual indicator comprising:
providing a material; and
providing a plurality of quantum dots adhering to the material, wherein the quantum dots are exposed on a surface of the material opposite an object when the material is attached to the object, the quantum dots fluorescing in response to the quantum dots being exposed to X-rays or gamma rays, wherein providing the visual indicator comprises attaching the visual indicator to a guide sleeve extending from a container for storing a gamma source, wherein the quantum dots fluoresce in response to the gamma source being outside of the container within the guide sleeve.

19. The method of claim 18, wherein providing the visual indicator comprises providing the visual indicator along a substantially complete extent of the guide sleeve and wherein only a portion of the quantum dots at a location of the gamma source within the guide sleeve fluoresce.

20. The method of claim 18, wherein providing the visual indicator comprises coating the guide sleeve with a paint containing the quantum dots.

\* \* \* \* \*